(12) United States Patent
Nimri

(10) Patent No.: US 11,975,116 B2
(45) Date of Patent: May 7, 2024

(54) ENTRYWAY SANITIZING ASSEMBLY

(71) Applicant: Lana Nimri, Houston, TX (US)

(72) Inventor: Lana Nimri, Houston, TX (US)

( * ) Notice: Subject to any disclaimer, the term of this patent is extended or adjusted under 35 U.S.C. 154(b) by 493 days.

(21) Appl. No.: 17/218,969

(22) Filed: Mar. 31, 2021

(65) Prior Publication Data
US 2022/0313846 A1 Oct. 6, 2022

(51) Int. Cl.
*A61L 2/00* (2006.01)
*A61L 2/24* (2006.01)

(52) U.S. Cl.
CPC .......... *A61L 2/0047* (2013.01); *A61L 2/0088* (2013.01); *A61L 2/24* (2013.01); *A61L 2202/11* (2013.01); *A61L 2202/14* (2013.01); *A61L 2202/15* (2013.01); *A61L 2202/20* (2013.01)

(58) Field of Classification Search
CPC ........ A61L 2/0047; A61L 2/0088; A61L 2/24; A61L 2202/11; A61L 2202/14; A61L 2202/15; A61L 2202/20; A61L 2202/122
See application file for complete search history.

(56) References Cited

U.S. PATENT DOCUMENTS

| | | | |
|---|---|---|---|
| 3,541,996 A | 11/1970 | Brockelsby | |
| 3,724,472 A | 4/1973 | Jenkins | |
| 5,255,695 A * | 10/1993 | Downey | B60S 3/04 |
| | | | 134/123 |
| 5,533,305 A | 7/1996 | Bielecki | |
| 6,277,207 B1 * | 8/2001 | Gauthier | B60S 3/042 |
| | | | 134/123 |
| 6,523,193 B2 | 2/2003 | Saraya | |
| 7,306,167 B2 | 12/2007 | Colarusso | |
| 9,427,774 B1 * | 8/2016 | Sheesley | B27K 5/003 |
| D812,247 S | 3/2018 | Price | |
| 2006/0163382 A1 | 7/2006 | Spivak et al. | |
| 2008/0289649 A1 * | 11/2008 | Woytkiw | B60S 3/00 |
| | | | 134/1 |
| 2009/0101174 A1 * | 4/2009 | Gaus | A47L 15/241 |
| | | | 134/107 |
| 2009/0211605 A1 * | 8/2009 | Ahmad | B60S 1/528 |
| | | | 134/123 |
| 2013/0087176 A1 * | 4/2013 | Sappington | B08B 9/28 |
| | | | 134/123 |
| 2020/0254122 A1 * | 8/2020 | Starkweather | A61L 2/10 |

(Continued)

FOREIGN PATENT DOCUMENTS

| | | | | |
|---|---|---|---|---|
| EP | 1201172 | | 10/2001 | |
| KR | 2014002307 U | * | 4/2014 | ............... A61L 2/10 |

*Primary Examiner* — Regina M Yoo

(57) ABSTRACT

An entryway sanitizing assembly for neutralizing microbes on an entrant includes a frame, which defines an opening through which a user can pass. A first sensor, which detect motion, is engaged to the frame and can detect a user approaching the opening. A lamp engaged to the frame emits ultraviolet radiation into the opening to neutralize microbes on the user passes through the opening. A plurality of nozzles is engaged to the frame and is directed into the opening. A pump is operationally engaged to the plurality of nozzles and to a reservoir containing a disinfectant solution. The disinfectant solution is pumped by the pump to the nozzles to generate a disinfectant mist to neutralize the microbes on the user passing through the opening. A controller selectively actuates the lamp and the pump upon detection of motion by the first sensor.

14 Claims, 4 Drawing Sheets

(56) References Cited

U.S. PATENT DOCUMENTS

2020/0306395 A1\* 10/2020 Gardiner ................... A61L 2/10
2022/0370671 A1\* 11/2022 Starkweather ......... G16H 40/20
2022/0370673 A1\* 11/2022 Ouni ......................... A61L 2/10

\* cited by examiner

ENTRYWAY SANITIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sanitizing assemblies and more particularly pertains to a new sanitizing assembly for neutralizing microbes on an entrant. The present invention discloses a motion activated sanitizing assembly that neutralized microbes by exposing the microbes to a combination of ultraviolet radiation and a disinfectant mist.

(2) Description of Related Art Including Information Disclosed Under 37 CFR 1.97 and 1.98

The prior art relates to sanitizing assemblies. The prior art includes motion sensor actuated liquid sprayers for animals, wherein the animals are sprayed with a solution, motion sensor actuated liquid sprayers for cleaning cars, light actuated misters to reduce insects in spaces, and manually activated spray booths for tanning. What is lacking in the prior art is a motion activated sanitizing assembly that neutralized microbes by exposing the microbes to a combination of ultraviolet radiation and a disinfectant mist.

BRIEF SUMMARY OF THE INVENTION

An embodiment of the disclosure meets the needs presented above by generally comprising a frame, which defines an opening that is configured for passage of a user. A first sensor, which is configured to detect motion, is engaged to the frame. The first sensor is configured to detect a user approaching the opening. A lamp is engaged to the frame and is configured to emit ultraviolet radiation into the opening. The lamp is configured to emit the ultraviolet radiation to neutralize microbes on a user passing through the opening. A plurality of nozzles is engaged to the frame and is directed into the opening. A pump is operationally engaged to the plurality of nozzles and to a reservoir containing a disinfectant solution. The pump is configured to pump the disinfectant solution to the nozzles to generate a disinfectant mist to neutralize the microbes on the user passing through the disinfectant mist in the opening. A controller is operationally engaged to the first sensor, the lamp, and the pump, so that, upon detection of motion by the first sensor, the controller is positioned to selectively actuate the lamp and the pump.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
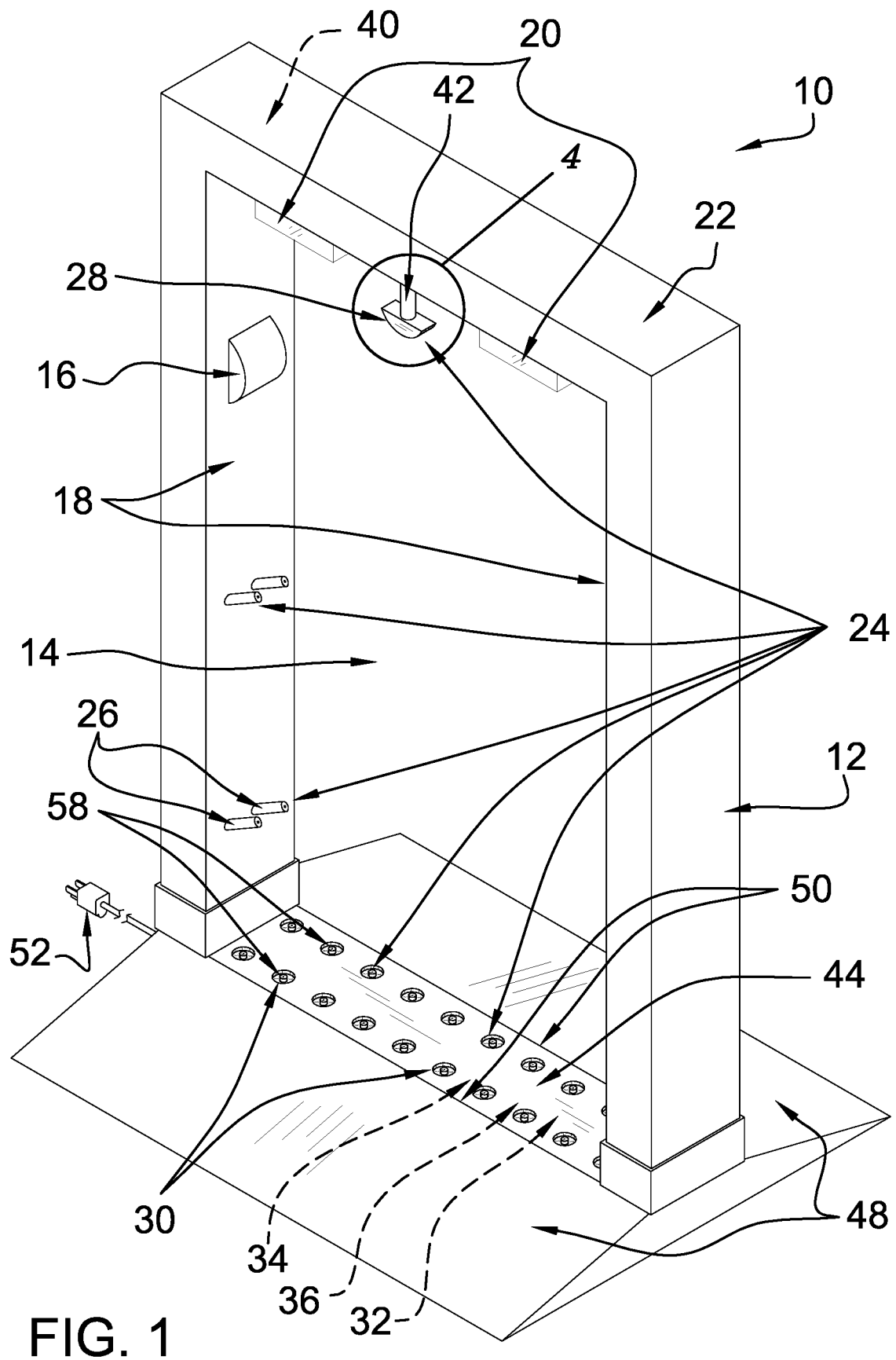
FIG. 1 is an isometric perspective view of an entryway sanitizing assembly according to an embodiment of the disclosure.

With reference now to the drawings, and in particular to FIGS. 1 through 4 thereof, a new sanitizing assembly embodying the principles and concepts of an embodiment of the disclosure and generally designated by the reference numeral 10 will be described.

As best illustrated in FIGS. 1 through 4, the entryway sanitizing assembly 10 generally comprises a frame 12, which defines an opening 14 that is configured for passage of a user. The frame 12 may be self-standing, as is shown in FIG. 1, or integral to a structure (not shown).

A first sensor 16, which is configured to detect motion, is engaged to the frame 12. The first sensor 16 is configured to detect a user approaching the opening 14. The first sensor 16 may be one of a pair of first sensors 16. The first sensors 16 of pair of first sensors 16 are engaged singly to opposed side elements 18 of the frame 12.

A lamp 20 is engaged to the frame 12 and is configured to emit ultraviolet radiation into the opening 14. The lamp 20 is configured to emit the ultraviolet radiation to neutralize microbes on a user passing through the opening 14. The lamp 20 is configured to emit ultraviolet radiation in a range of 200-280 nanometers. The lamp 20 may be one of a pair of lamps 20 engaged to an upper element 22 of the frame 12 so that ultraviolet radiation is emitted downwardly upon the user passing through the opening 14.

A plurality of nozzles 24 is engaged to the frame 12 and is directed into the opening 14. The plurality of nozzles 24 comprises a plurality of side misting units 26, a top misting unit 28, and a plurality of bottom misting units 30.

A pump 32 is operationally engaged to the plurality of nozzles 24 and to a reservoir 34 containing a disinfectant solution 36. The pump 32 is configured to pump the disinfectant solution 36 to the nozzles 24 to generate a disinfectant mist 38 to neutralize the microbes on the user passing through the disinfectant mist 38 in the opening 14.

Figure 2:
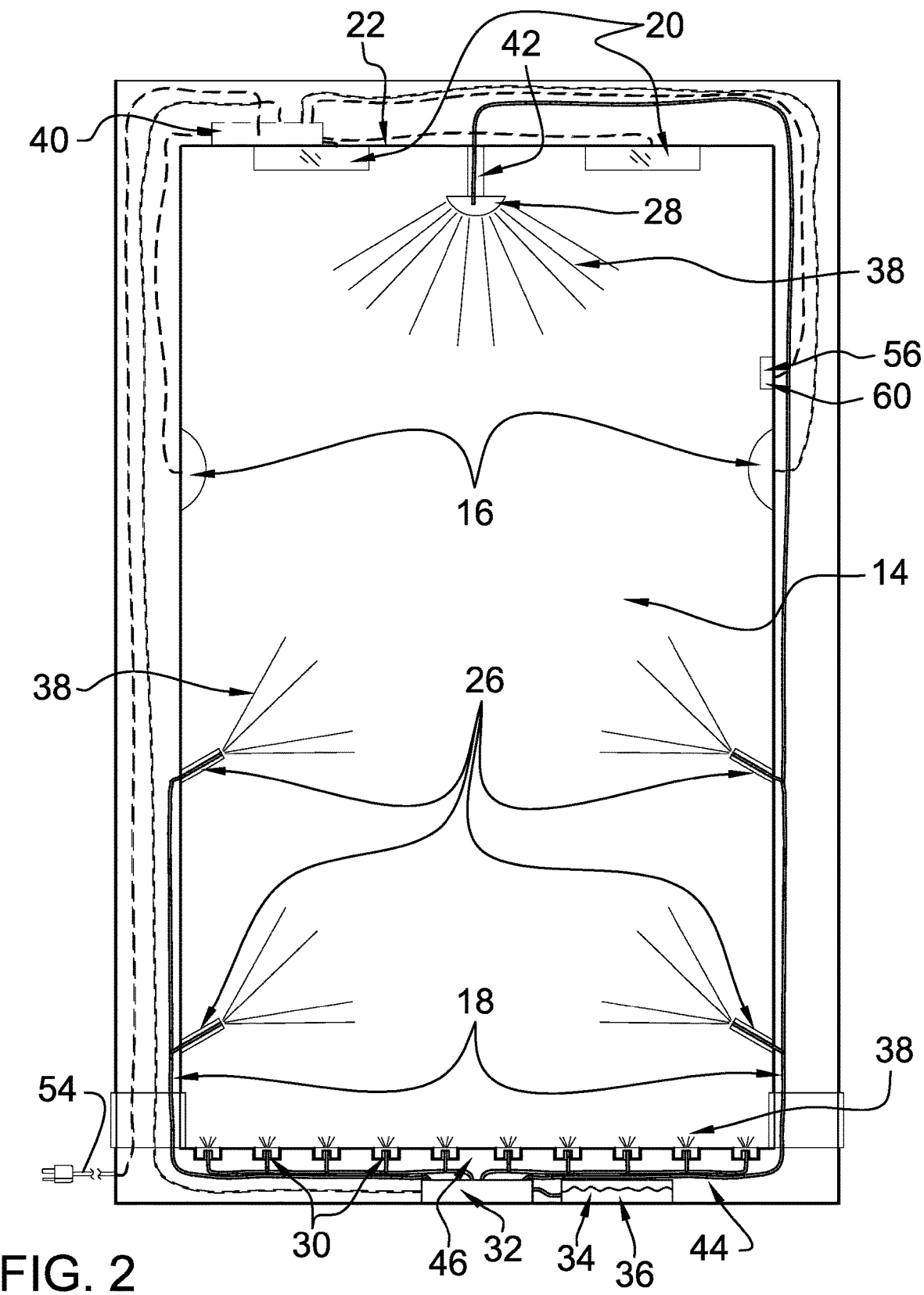
FIG. 2 is a front view of an embodiment of the disclosure.
Figure 3:
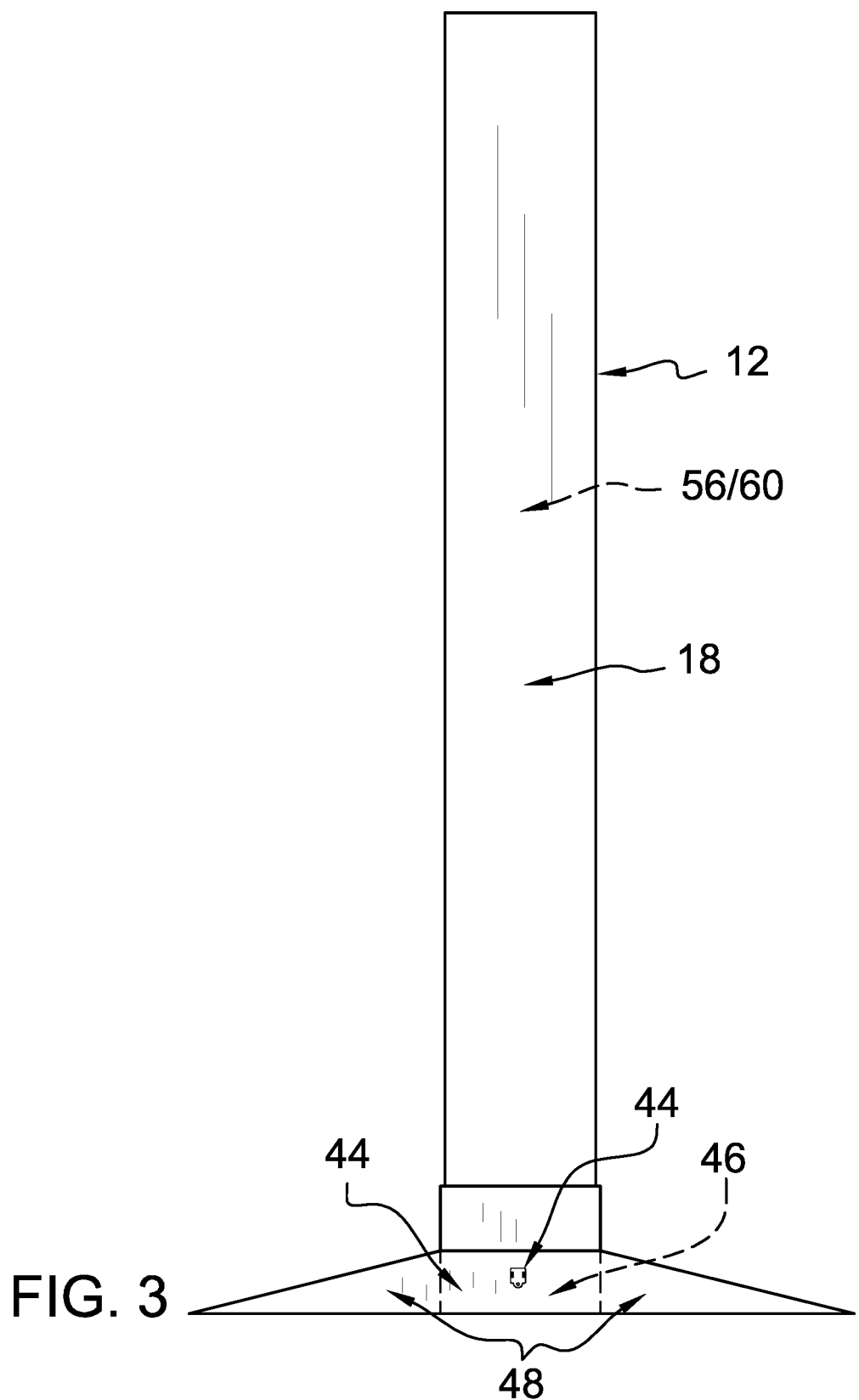
FIG. 3 is a side view of an embodiment of the disclosure.

A controller 40 is operationally engaged to the first sensor 16, the lamp 20, and the pump 32, so that, upon detection of motion by the first sensor 16, the controller 40 is positioned to selectively actuate the lamp 20 and the pump 32. The, the controller 40 may be engaged to the top element 22, as is shown in FIG. 2.

The side misting units 26 are engaged to the opposed side elements 18 of the frame 12 and are configured to direct disinfectant mist 38 bilaterally into the opening 14. The side misting units 26 may extend angularly from the opposed side elements 18 so that disinfectant mist 38 is directed angularly and upwardly from the opposed side elements 18 into the opening 14. The side misting units 26 are intended to direct disinfectant mist 38 onto the sides of the user.

Figure 4:
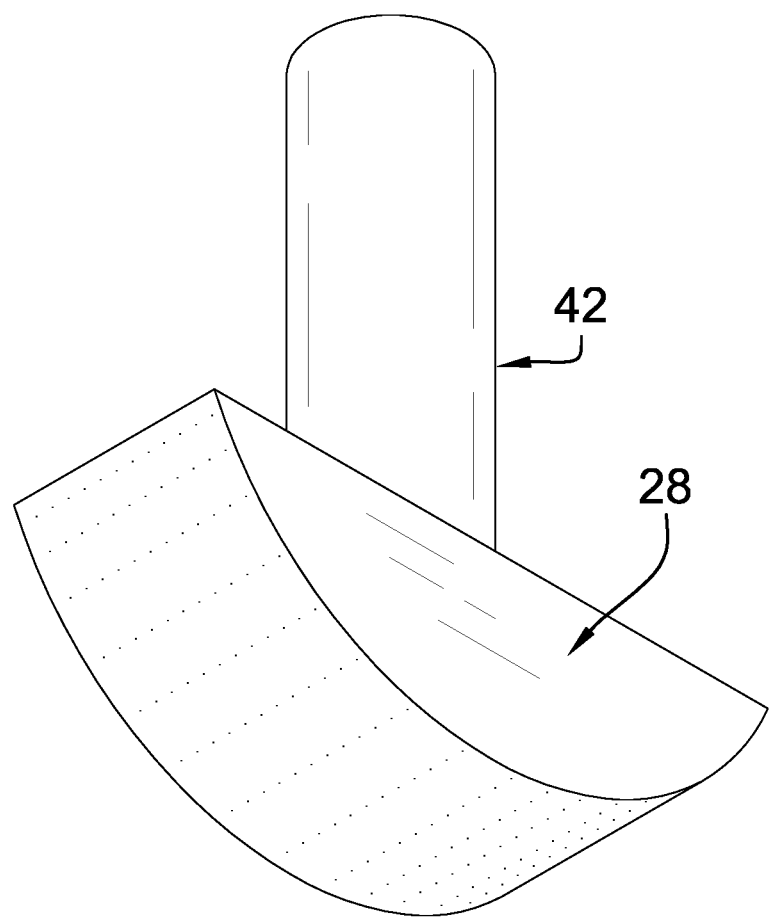
FIG. 4 is a detail view of an embodiment of the disclosure.

The top misting unit 28 is engaged to the upper element 22 and is configured to direct disinfectant mist 38 downwardly into the opening 14. The top misting unit 28 is intended to direct disinfectant mist 38 onto a head and shoulders of the user. A tube 42 may be engaged to the upper element 22 and extend downwardly from the upper element 22. The top misting unit 28 is engaged to the tube 42 distal from the upper element 22 so that disinfectant mist 38 emitted by the top misting unit 28 is below the lamp 20. This configuration aids in preventing accumulation of disinfectant mist 38 on the lamp 20. The top misting unit 28 may be partial disc shaped, as shown in FIG. 4, or may be alternatively shaped, such as, but not limited to, bar shaped, ring shaped, horizontal disc shaped, and the like.

The bottom misting units 30 are engaged to a threshold 44 of the frame 12 and are configured to direct disinfectant mist 38 upwardly into the opening 14. The bottom misting units 30 are intended to direct disinfectant mist 38 onto shoes of the user. The bottom misting units 30 may be positioned in a pair of rows 58, which extends substantially between the opposed side elements 18. The rows 58 of bottom misting units 30 are anticipated to improve contact of the disinfectant mist 38 with the shoes of the user relative to a single row.

The threshold 44 is hollow and defines an interior space 46 in which the reservoir 34 and the pump 32 are positioned, as is shown in FIG. 2. The present invention also anticipates the reservoir 34, the pump 32, and the controller 40 being positioned externally to the threshold 44.

The present invention also anticipates one or more drains being integral to, or positioned proximate to, the threshold 44. The drains would function to collect and direct runoff generated by accumulation of disinfectant mist 38. Additionally, the present invention anticipates one or more ventilation units positioned proximate to the assembly 10. The ventilation units would function to remove disinfectant mist 38 from the air outside of the opening 14. The present invention also anticipates a plurality of masks positioned proximate to the assembly 10 and being made available to users who are to pass through the opening 14. The masks may comprise activated carbon and would function to limit pulmonary exposure of the users to the disinfectant mist 38 as they pass through the opening 14.

Each of a pair of ramps 48 is engaged to and extends from a respective opposed side 50 of the threshold 44. The ramps 48 are configured to facilitate wheeled access through the opening 14. The present invention also anticipates the threshold 44 being substantially flush with a surface upon which the assembly 10 is positioned, in which case the ramps 48 would not be required.

A power module 52 is positioned in the interior space 46 and is operationally engaged to the controller 40 so that the controller 40 is positioned to selectively power the first sensor 16, the lamp 20, and the pump 32. The power module 52 may comprise a power cord 54, as is shown in FIG. 2, although the present invention also anticipates the assembly 10 being battery powered.

A second sensor 56 is engaged to a respective opposed side element 18 of the frame 12 and is operationally engaged to the controller 40. The second sensor 56 is configured to measure a temperature of the user as a means of assessing if the user has an infection. The second sensor 56 comprises an infrared thermometer 60, thermal imaging camera, or the like.

In use, as a user approaches the opening 14, the first sensor 16 detects the motion of the user and signals the controller 40, which actuates the lamp 20 and the pump 32. The lamp 20 emits the ultraviolet radiation into the opening 14 and the disinfectant solution 36 is pumped by the pump 32 to the nozzles 24 to generate a disinfectant mist 38 in the opening 14. Both the ultraviolet radiation and the disinfectant mist 38 work to neutralize the microbes on the user passing through the opening 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. An entryway sanitizing assembly comprising:
a frame defining an opening configured for passage of a user;
a first sensor engaged to the frame and being configured for detecting motion, wherein the first sensor is configured for detecting a user approaching the opening;
a lamp engaged to the frame and being configured for emitting ultraviolet radiation into the opening, wherein the lamp is configured for emitting ultraviolet radiation for neutralizing microbes on a user passing through the opening;
a plurality of nozzles engaged to the frame and being directed into the opening;
a reservoir containing a disinfectant solution;

a pump operationally engaged to the plurality of nozzles and the reservoir, wherein the pump is configured for pumping the disinfectant solution to the plurality of nozzles for generating a disinfectant mist for neutralizing the microbes on the user passing through the disinfectant mist in the opening;

a controller operationally engaged to the first sensor, the lamp, and the pump, such that, upon the first sensor detecting motion, the controller is positioned for selectively actuating the lamp and the pump;

wherein the plurality of nozzles comprises
a plurality of side misting units engaged to opposed side elements of the frame and being configured for directing mist bilaterally into the opening;
a top misting unit engaged to an upper element of the frame and being configured for directing mist downwardly into the opening; and
a plurality of bottom misting units engaged to a threshold of the frame and being configured for directing mist upwardly into the opening,
wherein the threshold is hollow such that the threshold defines an interior space;
wherein the reservoir and the pump being positioned in the interior space; and
wherein the controller being engaged to the upper element.

2. The entryway sanitizing assembly of claim 1, wherein the frame is self standing or integral to a structure.

3. The entryway sanitizing assembly of claim 1, wherein the first sensor is one of a pair of first sensors, the pair of first sensors being engaged singly to each one of opposed side elements of the frame.

4. The entryway sanitizing assembly of claim 1, wherein the lamp is configured for emitting ultraviolet radiation in a range of 200-280 nanometers.

5. The entryway sanitizing assembly of claim 1, wherein the lamp is one of a pair of lamps engaged to an upper element of the frame, such that ultraviolet radiation is emitted downwardly upon the user passing through the opening.

6. The entryway sanitizing assembly of claim 1, wherein the plurality of side misting units extends angularly from the opposed side elements, such that mist is directed angularly and upwardly from the opposed side elements into the opening.

7. The entryway sanitizing assembly of claim 1, further including a tube engaged to the upper element and extending downwardly from the upper element, the top misting unit being engaged to the tube distal from the upper element, such that mist emitted by the top misting unit is below the lamp.

8. The entryway sanitizing assembly of claim 1, wherein the plurality of bottom misting units is positioned in a pair of rows extending substantially between the opposed side elements.

9. The entryway sanitizing assembly of claim 1, further including a pair of ramps, each ramp being engaged to and extending from a respective opposed side of the threshold, wherein the pair of ramps is configured for facilitating wheeled access through the opening.

10. The entryway sanitizing assembly of claim 1, further including a power module positioned in the interior space and being operationally engaged to the controller, such that the controller is positioned for selectively powering the first sensor, the lamp, and the pump.

11. The entryway sanitizing assembly of claim 1, wherein the power module comprises a power cord.

12. The entryway sanitizing assembly of claim 1, further including a second sensor engaged to an associated one of a pair of opposed side elements of the frame, the second sensor being operationally engaged to the controller and being configured for measuring a temperature of the user.

13. The entryway sanitizing assembly of claim 12, wherein the second sensor comprises an infrared thermometer.

14. An entryway sanitizing assembly comprising:
a frame defining an opening configured for passage of a user, the frame being self standing or integral to a structure;
a first sensor engaged to the frame and being configured for detecting motion, wherein the first sensor is configured for detecting a user approaching the opening, the first sensor being one of a pair of first sensors, the pair of first sensors being engaged singly to each one of opposed side elements of the frame;
a lamp engaged to the frame and being configured for emitting ultraviolet radiation into the opening, wherein the lamp is configured for emitting ultraviolet radiation for neutralizing microbes on a user passing through the opening, the lamp being configured for emitting ultraviolet radiation in a range of 200-280 nanometers, the lamp being one of a pair of lamps engaged to an upper element of the frame, such that ultraviolet radiation is emitted downwardly upon the user passing through the opening;
a plurality of nozzles engaged to the frame and being directed into the opening, the plurality of nozzles comprising:
a plurality of side misting units engaged to the opposed side elements of the frame and being configured for directing mist bilaterally into the opening, the plurality of side misting units extending angularly from the opposed side elements, such that mist is directed angularly and upwardly from the opposed side elements into the opening,
a top misting unit engaged to the upper element and being configured for directing mist downwardly into the opening,
a tube engaged to the upper element and extending downwardly from the upper element, the top misting unit being engaged to the tube distal from the upper element, such that mist emitted by the top misting unit is below the lamp, and
a plurality of bottom misting units engaged to a threshold of the frame and being configured for directing mist upwardly, into the opening, the plurality of bottom misting units being positioned in a pair of rows extending substantially between the opposed side elements, the threshold being hollow such that the threshold defines an interior space;
a pair of ramps, each ramp being engaged to and extending from a respective opposed side of the threshold, wherein the pair of ramps is configured for facilitating wheeled access through the opening;
a reservoir containing a disinfectant solution;
a pump operationally engaged to the plurality of nozzles and the reservoir, wherein the pump is configured for pumping the disinfectant solution to the plurality of nozzles for generating a disinfectant mist for neutralizing the microbes on the user passing through the disinfectant mist in the opening;
a controller operationally engaged to the first sensor, the lamp, and the pump, such that, upon the first sensor detecting motion, the controller is positioned for selectively actuating the lamp and the pump, the reservoir; the pump, and the controller being engaged to the upper element;

a power module positioned in the interior space and being operationally engaged to the controller, such that the controller is positioned for selectively powering the first sensor, the lamp, and the pump, the power module comprising a power cord; and a second sensor engaged to a respective opposed side element of the frame, the second sensor being operationally engaged to the controller and being configured for measuring a temperature of the user, the second sensor comprising a infrared thermometer.

* * * * *